(12) United States Patent
Sayama et al.

(10) Patent No.: US 7,662,137 B2
(45) Date of Patent: Feb. 16, 2010

(54) DISPOSABLE DIAPER

(75) Inventors: Yasushi Sayama, Kagawa-ken (JP); Hironao Minato, Kagawa-ken (JP); Koichiro Tani, Kagawa-ken (JP); Koichiro Mitsui, Kagawa-ken (JP); Kengo Ochi, Kagawa-ken (JP); Masato Isono, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 1179 days.

(21) Appl. No.: 10/720,488

(22) Filed: Nov. 25, 2003

(65) Prior Publication Data

US 2004/0111076 A1    Jun. 10, 2004

(30) Foreign Application Priority Data

Dec. 4, 2002    (JP) .............................. 2002-353001

(51) Int. Cl.
  *A61F 13/15*    (2006.01)
  *A61F 13/20*    (2006.01)
(52) U.S. Cl. .................. 604/386; 604/389; 604/391
(58) Field of Classification Search ............ 604/385.01, 604/385.02–6, 387, 386, 389, 391
  See application file for complete search history.

(56) References Cited

U.S. PATENT DOCUMENTS

| | | | |
|---|---|---|---|
| 5,151,230 A * | 9/1992 | Damberg ..................... 264/83 |
| 5,858,013 A * | 1/1999 | Kling .......................... 604/386 |
| 6,099,516 A * | 8/2000 | Pozniak et al. .............. 604/386 |
| 6,755,809 B2 * | 6/2004 | Kline et al. .................. 604/390 |
| 6,905,488 B2 * | 6/2005 | Olson .......................... 604/389 |
| 2003/0114826 A1 * | 6/2003 | Roessler et al. ........ 604/385.28 |
| 2003/0124928 A1 * | 7/2003 | Sherrod et al. ................ 442/76 |

FOREIGN PATENT DOCUMENTS

JP    63-256702 A    10/1988

OTHER PUBLICATIONS (1) http://www.tfxmedical.com/reference/materials.htm.*
(2) http://www.machinist-materials.com/comparison_table_for_plastics.htm.*

* cited by examiner

*Primary Examiner*—Melanie J Hand
(74) *Attorney, Agent, or Firm*—Lowe Hauptman Ham & Berner

(57) ABSTRACT

A disposable diaper is formed in one of front and rear waist regions with first wings which are elastically stretchable in a waist-surrounding direction and these first wings are provided on respective body facing surfaces with first fastener elements. The other waist region is provided on its undergarment facing surface with, in addition to second fastener elements, anti-slip zones exhibiting a desired average kinetic frictional force relative to the body facing surface of the first wings.

20 Claims, 5 Drawing Sheets

DISPOSABLE DIAPER

RELATED APPLICATIONS

The present application is based on, and claims priority from, Japanese Application Serial Number 2002-353001, filed Dec. 4, 2002, the disclosure of which is hereby incorporated by reference herein in its entirety.

BACKGROUND OF THE INVENTION

The present invention relates to a disposable diaper.

In open-type disposable diapers, it is well known to provide at least one of an undergarment facing surface of wings in a front waist region and a body facing surface of wings in rear waist region with anti-slip members in order to alleviate a slippage possibly occurring between these two facing surfaces. For example, Japanese Laid-Open Patent Application No. 1988-256702 A discloses a disposable diaper exhibiting a static friction coefficient of 0.8 or higher between these two surfaces. To achieve such friction coefficient, at least one of these two surfaces is coated with an adhesive, acrylic anti-slip agent, urethane sheet or the like.

With the diaper disclosed in the above-cited Application put on a wearer's body, the front and rear wings placed upon each other along lateral zones of front and rear waist regions are reliably prevented from shifting and/or twisting relative to each other and leakage of bodily discharges is also reliably prevented. However, any effective measure can not be found in this diaper of well known art to make these wings placed upon each other smoothly follow movement of the wearer's body. Consequently, the lateral zones of the front and rear waist regions put on the wearer's body are relatively stiff and hardly stretchable, inevitably creating a feeling of discomfort against the wearer.

SUMMARY OF THE INVENTION

In view of the problem as has been described above, it is an object of the present invention to improve the above-described diaper of well known art so that a comfortable feeling to wear the diaper can be maintained even when transversely opposite lateral zones of front and rear waist regions are placed upon each other.

According to the present invention, there is an open-type disposable diaper configured by a front waist region, a rear waist region and a crotch region extending between these two waist regions, these regions having a body facing surface and an undergarment facing surface opposed to the body facing surface, the diaper being contoured by front and rear end zones extending in parallel to each other in a waist-surrounding direction and transversely opposite lateral zones extending in parallel to each other in back-and-forth direction crossing the waist-surrounding direction, the transversely opposite lateral zones in one of the front and rear waist regions being formed with first wings extending in the waist-surrounding direction, the first wings are respectively provided on the body facing surface with first fastener means and the undergarment facing surface in the other of the front and rear waist regions being provided with second fastener means on which the first fastener means are detachably anchored.

The invention further comprises the first wings being elastically stretchable in the waist-surrounding direction and the undergarment facing surface in the other waist region being provided in a vicinity of the second fastener means with anti-slip zones each adapted to come in contact with the body facing surface of the wings and to exhibit an average kinetic frictional force of 0.5 N or higher under a load of 58.23 g/9 $cm^2$ and an average kinetic frictional force of 5 N or lower under a load of 340 g/9 $cm^2$ relative to the body facing surface as the first fastener means are anchored on the second fastener means.

The present invention includes the following embodiments.

The transversely opposite lateral zones in the crotch region is provided with leg elastic members extending further into the front and rear waist regions and the anti-slip zones are formed so as to cover parts of the leg elastic members or so as to lie on respective extensions of the leg elastic members in said back-and-forth direction.

The anti-slip zones are formed so as to be placed aside from the lateral zones toward a center line bisecting a width of the diaper and there are provided between respective the anti-slip zones and respective the lateral zones slip-zones each exhibiting an average kinetic frictional force lower than the average kinetic frictional force exhibited by each of the anti-slip zones.

Elastic fibers made of a plastic elastomer and having a fiber length of 5 to 100 mm are mixed with inelastic fibers made of a thermoplastic material having a fiber length of 5 to 100 mm in the anti-slip zones.

Continuous elastic fibers made of a plastic elastomer are mixed with continuous inelastic fibers made of a thermoplastic material in the anti-slip zones.

A weight ratio of the elastic fibers and inelastic fibers in the anti-slip zone is in a range of 8:2 to 5:5.

The anti-slip zone is formed by bonding the elastic fibers and inelastic fibers mixed together to any one of a nonwoven fabric, woven fabric and film.

The inelastic fiber and the nonwoven fabric contain thermoplastic material having substantially same melting points while the woven fabric and film contain thermoplastic material having substantially the same melting points.

The lateral zones are partially broadened in the waist-surrounding direction to form second wings in the other waist region and the anti-slip zones are formed so as to be placed aside from distal end portions of the second wings toward the center line bisecting the width of the diaper.

The second wing is provided in a zone placed aside to the distal end portion with a slip-zone having the average kinetic frictional force lower than that of the anti-slip zone.

In this invention, the average kinetic frictional force is measured using the method prescribed paragraph 3.1 of JIS (Japanese Industrial Standard) P 8147. A weight of 3 cm×3 cm and adapted to apply a load of 58.23 g/9 $cm^2$ or 340 g/9 $cm^2$ is used to carry out this measurement. Moving velocity of the weight is set to 10 cm/min. This measuring method will be described more in detail with reference to FIG. 5 of the accompanying drawings. An entire area of a sheet 102 defining the body facing surface in the first wings of the disposable diaper is fixed to a smooth upper surface of a fixed plate 101 by means of double-faced adhesive tape (not shown). A movable plate 103 has its lower surface of 3 cm×3 cm and a total weight of this movable plate 103 is adjusted by a weight W so that a load of 58.23 g/9 $cm^2$ or 340 g/9 $cm^2$ is applied to the lower surface. Such movable plate is used as the weight. Then the movable plate 103 is pulled in a direction indicated by an arrow Y and thereby moved by 5 cm. An average kinetic frictional force (unit: N) is calculated from values of frictional force measured in the course of this movement.

DETAILED DESCRIPTION OF THE PREFERRED EMBODIMENTS

Details of a disposable diaper according to the present invention will be more fully understood from the description given hereunder with reference to the accompanying drawings.

Figure 1:
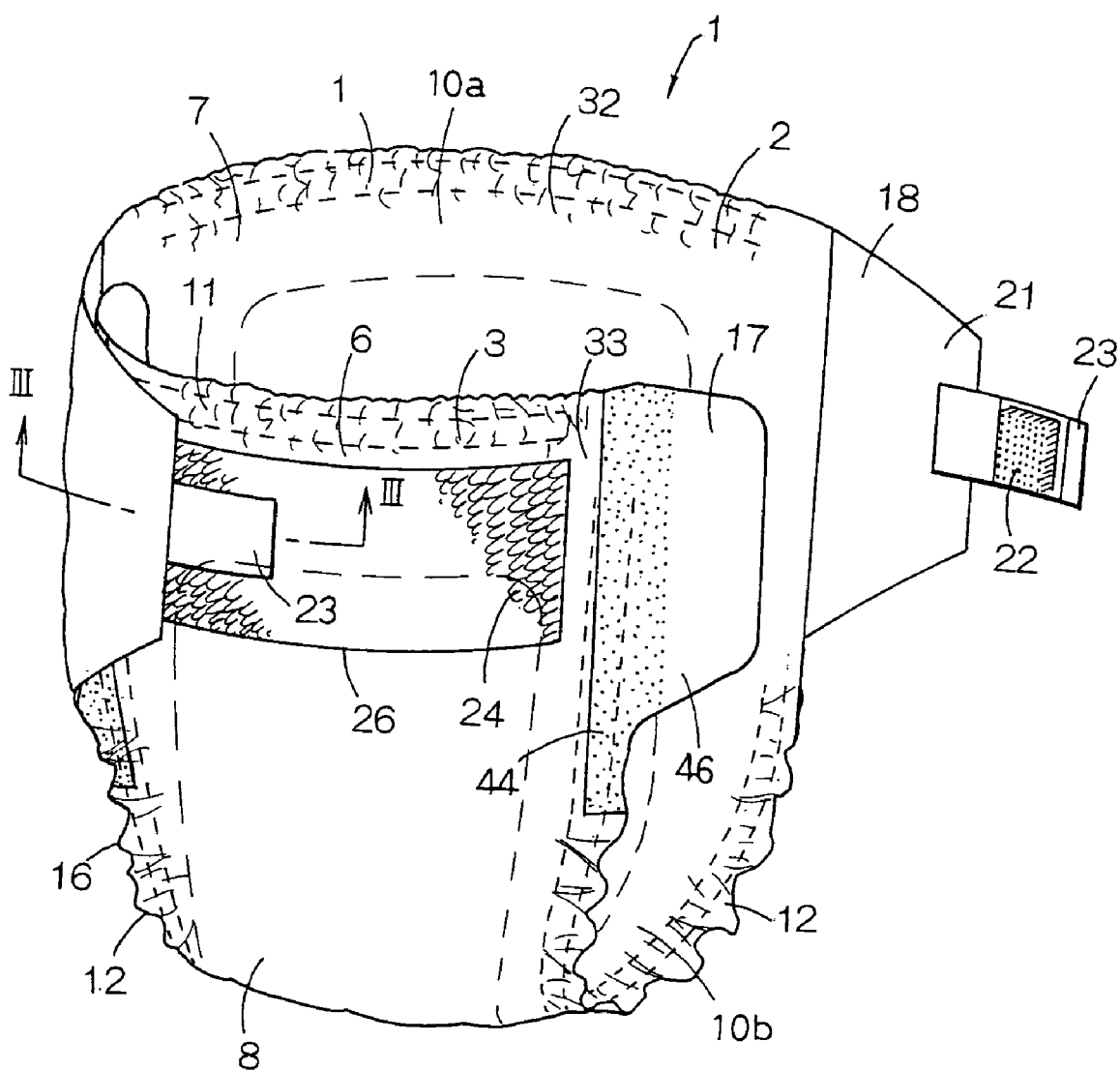
FIG. 1 is a perspective view of a disposable diaper according to the present invention.
Figure 2:
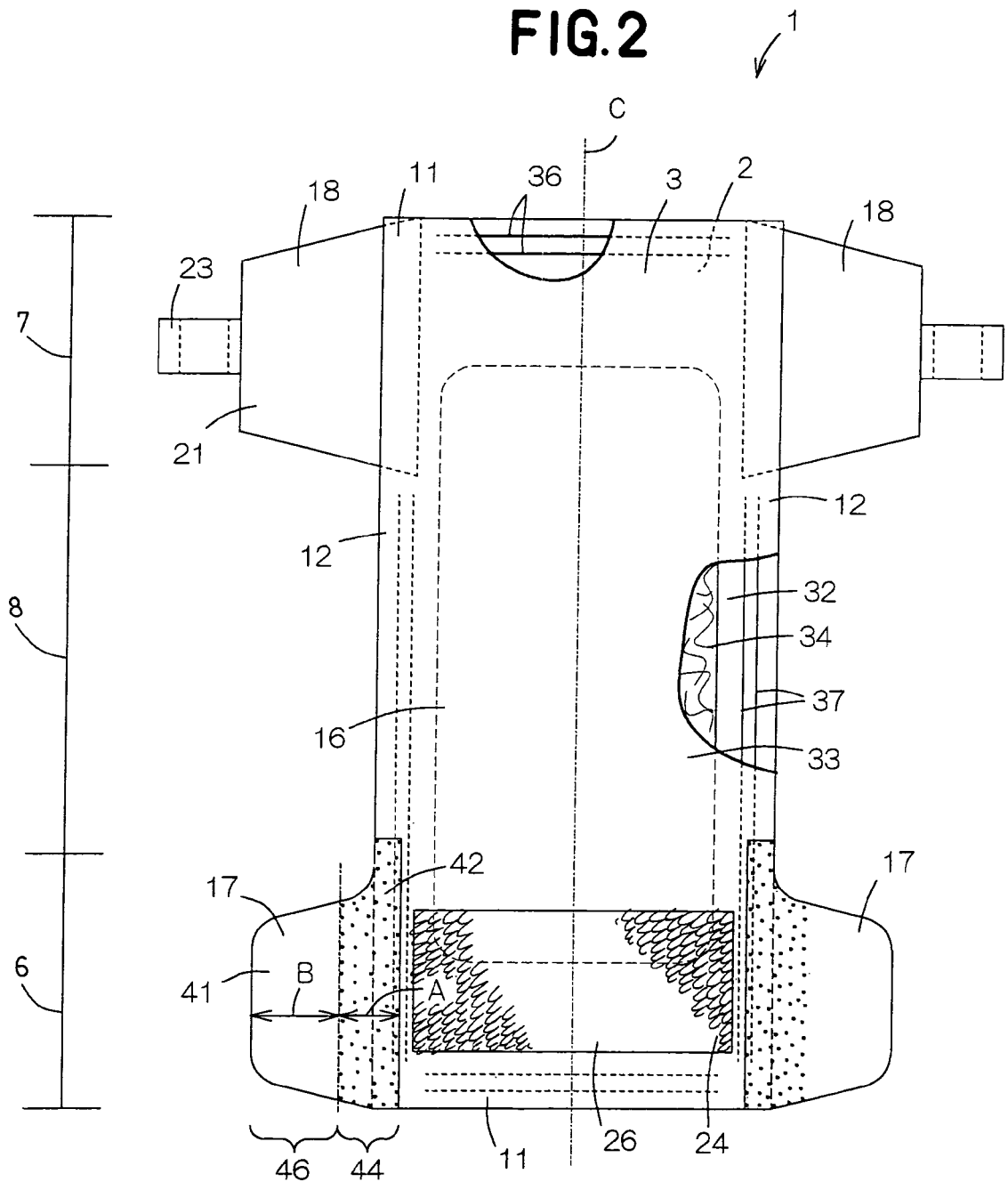
FIG. 2 is a developed plan view of the disposable diaper.

FIG. 1 is a perspective view of an open-type disposable diaper 1 according to the present invention as put on a wearer's body and FIG. 2 is a developed and partially cutaway plan view of the disposable diaper 1. Referring to FIG. 2, a center line C bisects a width of the diaper 1. The diaper 1 is of open-type and has a surface 2 facing a wearer's body and a surface 3 facing a wearer's undergarment. As viewed in a back-and-forth direction, the diaper 1 is composed of a front waist region 6, a rear waist region 7 and a crotch region 8 extending between these waist regions 6, 7. The diaper 1 is contoured by a pair of waist-surrounding upper end zones 11 and a pair of lateral zones 12 extending in the back-and-forth direction (i.e., in vertical direction as viewed in FIG. 2) so as to cross these waist-surrounding upper end zones 11. FIG. 1 illustrates the diaper 1 with the surface 2 facing the wearer's body inside and with the surface 3 facing the wearer's undergarment outside. FIG. 2 illustrates the diaper 1 with the undergarment facing surface 3 on upper side and with the body facing surface 2 on a rear side.

As will be seen in FIG. 2, the diaper 1 has a rectangular body section 16, a pair of front wings 17 extending in a waist-surrounding direction from transversely opposite lateral zones of the front waist region 6 in the body section 16 and a pair of rear wings 18 extending in the waist-surrounding direction from transversely opposite lateral zones of the rear waist region 7 in the body section 16. A pair of tape fasteners 23 extends from distal end portions 21 of the respective rear winds 18, each of these tape fasteners 23 including a hook member 22 (See FIG. 3) which is one component constituting the so-called mechanical fastener commonly known, for example, of the trademark "VELCRO". These tape fasteners 23 extend in the waist-surrounding direction and serve as first fastener means. The front waist region 6 in the body section 16 is formed on the undergarment facing surface 3 with a landing zone 26 which is provided with a loop member 24 (See FIG. 3), the other component constituting the mechanical fastener. This landing zone 26 serves as second fastener means. To put such diaper 1 on the wearer's body, the front waist region 6 may be placed against the belly side of the wearer, the rear waist region 7 may be placed against the wearer's back side, then the rear wings 18 may be placed from outside upon the front wings 17, the tape fasteners 23 may be pulled in the waist-surrounding direction and anchored on the landing zone 26. The tape fasteners 23 and the landing zone 26 are substantially fixed one to another without an anxiety that these tape fasteners 23 and landing zone 26 might be shifted relative to one another or peeled off one from another. Upon wearing the diaper in this manner, the diaper 1 is formed with a waist-hole 10a and a pair of leg-holes 10b.

The body section 16 shown by FIG. 2 comprises a liquid-pervious topsheet 32 defining the body facing surface 2, a liquid-impervious backsheet 33 defining the undergarment facing surface 3 and a liquid-absorbent core 34 interposed between these two sheets 32, 33. Portions of the top- and backsheets 32, 33 extending outward beyond a peripheral edge of the core 34 are joined together by means of adhesion or heat-sealing. Along the portions of the top- and backsheets 32, 33 put flat together, waist elastic members 36 extending in the waist-surrounding direction in stretched state and leg elastic members 37 extending over the crotch region 8 into the front and rear waist regions 6, 7 in stretched state are interposed between the top- and backsheets 32, 33 and joined to the inner surface of at least one the top- and backsheets 32, 33 by means of adhesives (not shown).

Figure 3:
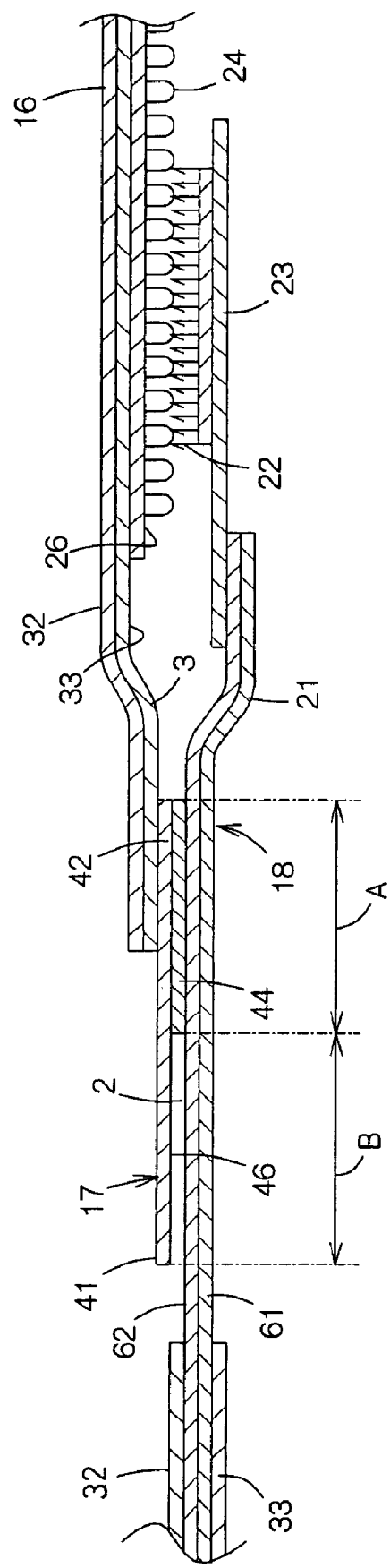
FIG. 3 is a sectional view taken along line III-III in FIG. 1.

FIG. 3 is a sectional view taken along line III-III in FIG. 1. Each of the front wings 17 shown in FIG. 3 is formed by sheet materials such as a nonwoven fabric, woven fabric or plastic film, preferably by a breathable sheet material and more preferably by a breathable and sweat-absorbent sheet material. Each of the front wings 17 has a distal end portion 41 being remote from the center line C (See FIG. 2) in the waist-surrounding direction and a proximal end portion 42 located aside toward the center line C and joined to the surface 3 facing the wearer's undergarment of the body section 16 by means of heat-sealing or adhesion. The proximal end portion 42 immediately overlies the associated leg elastic members 37 so as to cover end zone of these members 37 or overlies extension of the associated leg elastic members 37 as viewed in the back-and-forth direction (See FIG. 2). The proximal end portion 42 is formed in its zone adjacent the landing zone 26 with a anti-slip zone 44 as indicated by a plurality of spots in FIG. 2. Each of the front wings 17 is formed in its zone located aside toward the distal end portion 41 relative to the anti-slip zone 44 with a slip zone 46. In the illustrated embodiment, the anti-slip zone 44 has a dimension A in a range of 5 to 70 mm in the waist-surrounding direction and the slip zone 46 has a dimension B in a range of 0 to 50 mm in the waist-surrounding direction. The anti-slip zone 44 exhibits an average kinetic frictional force of 0.5 N or higher under a load of 58.23 g/9 cm$^2$ and an average kinetic frictional force of 5 N or lower under a load of 340 g/9 cm$^2$. The slip zone 46 exhibits an average kinetic frictional force lower than 0.5 N, preferably less than 0.3 N under a load of 58.23 g/9 cm$^2$.

To realize the front wings 17 having such anti-slip zones 44, after a basic body of the front wing 17 has been formed, for example, by a nonwoven fabric made of polypropylene continuous fibers having a fineness in range of 1 to 4 dtex and a basis weight in a range of 30 to 100 g/m$^2$, the proximal end portions 42 thereof are joined to the transversely opposite lateral zones of the body section 16. The sheet-like fibrous mixture consisting of elastic fibers of styrene-based block copolymer such as SEBS, SEPS or SBBS having a fineness in a range of 0.1 to 3 dtex and inelastic fibers such as polypropylene-based fibers having a fineness in a range of 0.1 to 3 dtex may be placed upon and intermittently heat-sealed to desired zones of the nonwoven fabric. In each of such front wings 17, the zone having no fibrous mixture placed thereupon defines the slip zone 46. In the anti-slip zone 44, the elastic fibers constituting the fibrous mixture and exposed outward exhibits a sufficiently high average kinetic frictional force to resist slippage of a counterpart coming in contact with this anti-slip zone 44. As will be understood from this example, the sheet material such as nonwoven fabric used to form the basic body of the front wing 17 preferably contains plastic ingredient exhibiting a substantially the same melting point as that of the inelastic fibers contained in the anti-slip zone 44. More preferably, the sheet material forming the basic body of the front wing 17 contains the exactly same plastic ingredient as the plastic ingredient of the inelastic fibers constituting the anti-slip zone 44.

The elastic fibers and the inelastic fibers are mixed with each other at a weight ratio in a range of 8:2 to 5:5. The content of the elastic fibers in the mixture may be appropriately selected to vary a total area of the elastic fibers exposed toward the rear wings 18 destined to be put flat together with the anti-slip zones 44 when the diaper 1 is put on the wearer's body. Larger the total area of the elastic fibers is, higher the average kinetic frictional force of the anti-slip zones 44 is. On the contrary, larger the total area of the inelastic fibers is, lower the average kinetic frictional force of the anti-slip zones 44 is. If the content of the elastic fibers in the fibrous mixture exceeds 80%, the average kinetic frictional force will be too high to raise the elastic fibers. If the content of the elastic fibers in the fibrous mixture is less than 50%, the average kinetic frictional force will be excessively low and consequently the rear wing 18 will be apt to slip relative to the associated front wing 17. The inelastic elastic fibers in the anti-slip zone 44 may be heat-sealed with the sheet material constituting the associated front wing 17 to ensure that the elastic fibers mixed with the inelastic fibers can be firmly fixed to the sheet material. When the plastic ingredient of these inelastic fibers has a melting point approximate to a melting point exhibited by the plastic ingredient in the sheet material forming the basic body of the front wing 17, the elastic fibers can be reliably fixed to the sheet material. When the plastic ingredient contained in the sheet material forming the basic body of the front wing 17 is exactly the same as the plastic ingredient contained in the anti-slip zone 44, the elastic fibers can be more reliably fixed to the sheet material. In this way, it is not concerned that the elastic fibers might be raised on and/or fall off from the front wing 17 even when the elastic fibers is pulled by the rear wing 18 which is closely in contact with the elastic fibers.

In the anti-slip zone 44, the elastic fibers as well as the inelastic fibers may be used in form of continuous fibers or short fibers having a length of 5 to 100 mm. The anti-slip zone 44 formed by the continuous elastic fibers and the continuous inelastic fibers is advantageous in that the anti-slip zone 44 can be prevented from fluffing but disadvantageous in that the mixing ratio of the elastic fibers and the inelastic fibers is not necessarily reflected in the exposed area ratio of the elastic fibers and the inelastic fibers. This is for the reason that it is difficult for these two types of continuous fibers to be evenly mixed and often one of them is more significantly exposed than the other. In addition to such problem, even when each of these continuous fibers is bonded at a plurality of spots thereof to the sheet material forming the front wing 17, this fiber may be peeled off from the sheet material successively at the respective spots once this fiber has been peeled off at one of these spots.

The anti-slip zone 44 formed by the elastic fibers and the inelastic fibers both of which are short fibers is inconvenient in that a plurality of heat-sealing spots must be provided to bond these two types of fibers to the sheet material forming the front wing 17. However, these two types of fibers can be easily mixed with each other and the mixing ratio of them is faithfully reflected in the exposed area ratio of the elastic fibers and the inelastic fibers. In addition, should one of these short fibers be peeled off from the front wing 17 at its bonded spot, there is no anxiety that any other fiber might be affected thereby to be easily peeled off from the front wing 17. Furthermore, many distal ends of the short fibers present on the anti-slip zone 44 tightly enter into interstices of the fibers on the rear wing 18 put flat together with the associated front wing 17 and function to enhance the average kinetic frictional force.

Referring to FIG. 3, each of the rear wings 18 is elastically stretchable in the waist-surrounding direction and comprises a base sheet 61 formed by a nonwoven fabric made of plastic elastomer or film made of plastic elastomer and a fibrous layer 62 adapted to follow stretching and contraction of the base sheet 61 and to define a body facing surface and/or an undergarment facing surface of the base sheet 61. The fibrous layer 62 is preferably formed by inelastic fibers to ensure that the rear wing 18 is adequately slippery relative to the wearer's body. It is possible to form the fibrous layer 62 by crimped conjugate fibers or to provide the fibrous layer 62 with undulations in the waist-surrounding direction to ensure that the base sheet 61 can be smoothly stretched and contracted.

After the diaper 1 of such construction has been put on the wearer's body with the tape fasteners 23 anchored on the landing zone 26, the front wings 17 are prevented from easily slipping relative to the respective anti-slip zones 44 since each of these anti-slip zones 44 has an average kinetic frictional force of 0.5 N or higher under a load of 58.23 g/9 cm2 relative to the respective rear wings 18 put flat together with the respective the front wings 17. In other words, the front wing 17 is semi-fixed to the body facing surface 2 of the associated rear wing 18 by means of the anti-slip zone 44 provided on this front wing 17 and there is no fear that the front wing 17 might shift and/or twist relative to the associated rear wing 18 put flat together with the this front wing 17 during use of the diaper 1. While the rear wing 18 is elastically stretchable under normal circumstances, it is difficult for the rear wing 18 to be easily stretchable in its zone placed upon the anti-slip zone 44. However, the rear wing 18 can be easily stretchable in its zone put flat together with the slip zone 46 and effectively function expected for the elastic rear wing 18. The average kinetic frictional force between the anti-slip zone 44 and the zone of the rear wing 18 put flat together therewith may be adjust to be 5 N or less under a load of 340 g/9 cm2 to ensure that the rear wing 18 can slip relative to the associated anti-slip zone 44 as the rear wing 18 is intentionally pulled so that the front and rear waist regions 6, 7 might be counterchanged in the waist-surrounding direction. With a consequence, this diaper 1 is free from a problem that the presence of the anti-slip zones 44 might uncomfortably tighten the wearer's waist.

The anti-slip zone 44 provided on the front wing 17 puts flat together with the associated rear wing 18 in such manner as has been described above and thereby prevents the front wing 17 as well as the rear wing 18 from being forcibly deformed. The range in which the anti-slip zone 44 is formed is not limited to that as illustrated but may be further enlarged. For example, the anti-slip zone 44 may extend to the distal end portion 41 of the front wing 17 and, if desired, the anti-slip zone 44 may extend over the entire area of the backsheet 33. However, the distal end portion 41 of the front wing 17 is preferably left for formation of the slip-zone 46 to avoid the inconvenience that the elastic stretch of the rear wing 18 might be constricted. The anti-slip zone 44 is preferably formed immediately above or on extension of the leg elastic members 37 as will be seen in FIGS. 1 and 2 so that the leg elastic members 37 cooperate with the rear wing 18 to form an elastically stretchable continuous ring adapted to surround the wearer's leg through the intermediary of the anti-slip zone 44. In this way, a fitness around the wearer's legs is improved and leak of bodily fluids can be prevented.

Figure 4:
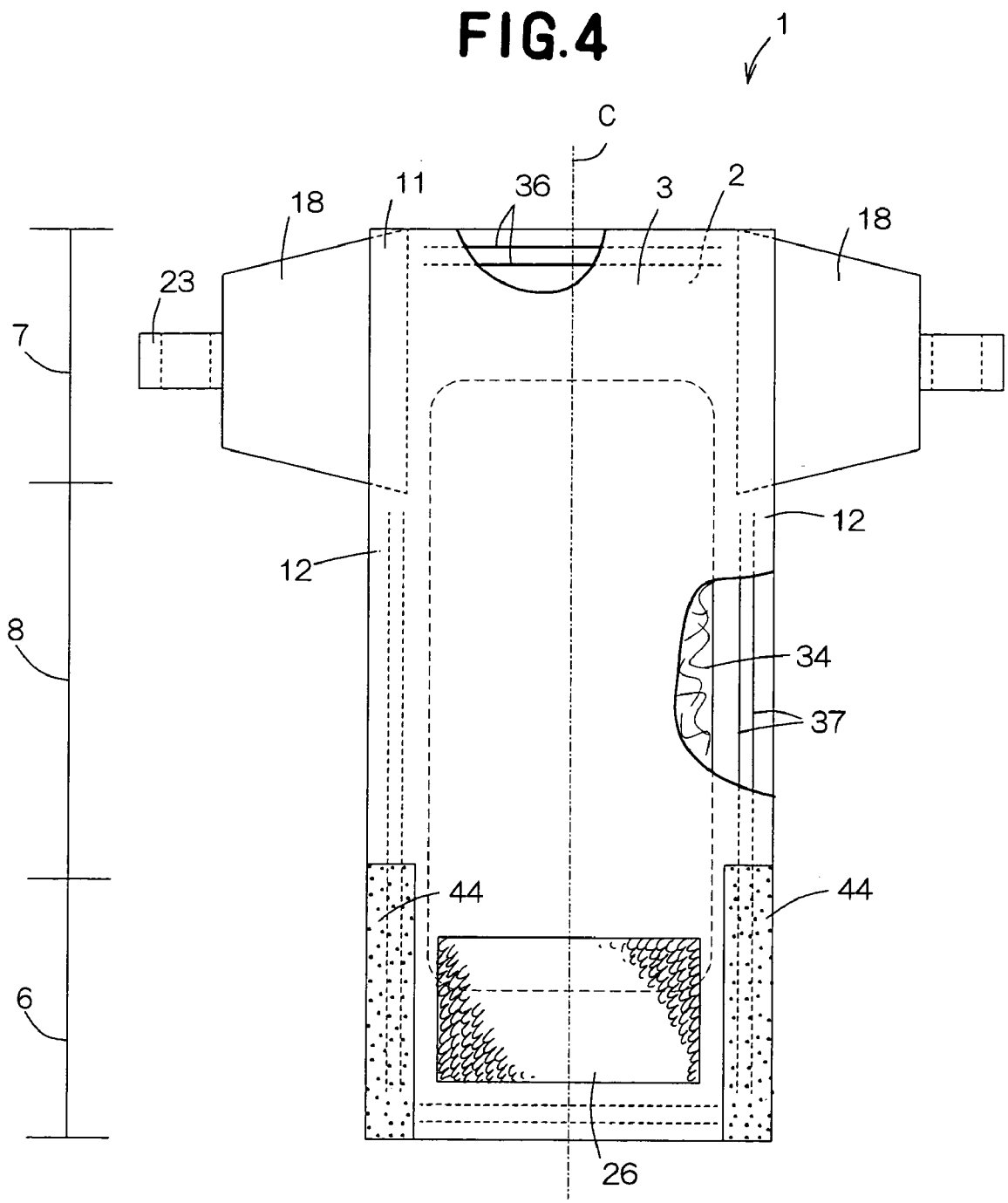
FIG. 4 is a view similar to FIG. 2, of a disposable diaper according to one preferred embodiment of the present invention.
Figure 5:
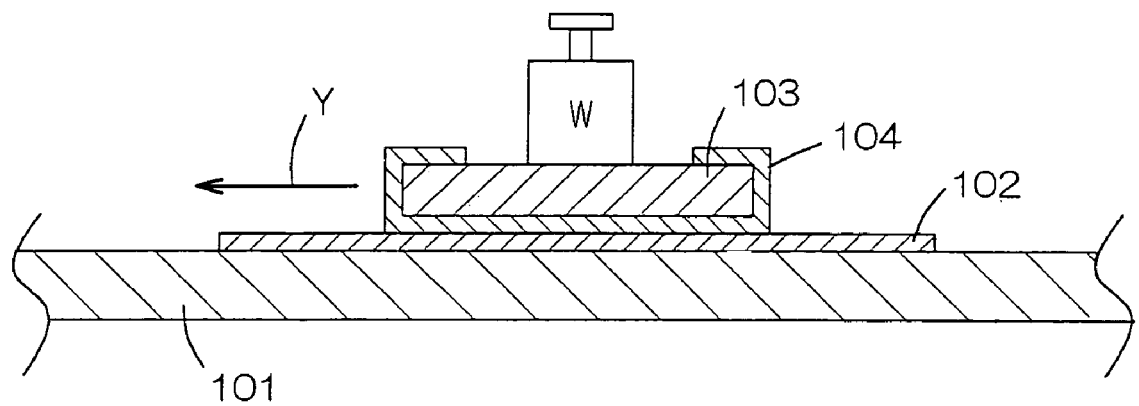
FIG. 5 is a diagram illustrating a method for measurement of an average kinetic frictional force.

FIG. 4 is a view similar to FIG. 2, showing the disposable diaper 1 according to one preferred embodiment of the present invention. The diaper 1 according to this embodiment is distinguished from the previously described embodiment in that the diaper 1 has the rear wings 18 but not the front wings 17 and the transversely opposite lateral zones 12 rectilinearly extend from the crotch region 8 toward the front waist region 6, on one hand, and diverge in the waist-surrounding direction in the rear waist region 7 so as to form the rear wings 18. In the case of this diaper 1, the anti-slip zones 44 are formed on the undergarment facing surface 3 of the lateral zones 12 in the front waist region 6 and the landing zone 26 is formed between these anti-slip zones 44. The rear wings 18 are similar to those illustrated by FIG. 2 and elastically stretchable.

As a variant of the embodiment illustrated by FIGS. 1 and 2, the present invention can be implemented in the form of a diaper wherein each of the front wings 17 is elastically stretchable in the waist-surrounding direction and provided with the tape fasteners 23 and the rear wings 18 are inelastic and provided on the undergarment facing surface 3 in the vicinity of the proximal end portions thereof with the anti-slip zones 44. As a variant of the embodiment illustrated by FIG. 4, the present invention can be implemented in the form of a diaper wherein the front wings are elastically stretchable and provided with the tape fasteners and there is provided none of the rear wings. Furthermore, the hook members 22 on the tape fasteners 23 serving as the first fastener means may be replaced by a pressure-sensitive adhesive and the backsheet 33 defining the undergarment facing surface 3 of the front waist region 6 serves as the second fastener means.

The disposable diaper according to the present invention is in that the undergarment facing surface in one of the front and rear waist regions is provided with the anti-slip zones and the landing zone inside both anti-slip zones and the other of the front and rear waist regions is formed with the wings which are elastically stretchable in the waist-surrounding direction so that the undergarment facing surface of these wings may be put flat together with the anti-slip zones. Such an arrangement is effective to prevent the vicinity of the anti-slip zones and the wings put flat together therewith from shifting and twisting relative to each other. In addition, The portions of the wings put flat together with the anti-slip zones also are stretchable in the waist-surrounding direction as these wings are intentionally pulled in the waist-surrounding direction and therefore it is not concerned that these wings might uncomfortably-tighten the wearer's waist.

What is claimed is:

1. An open-type disposable diaper configured by a front waist region, a rear waist region and a crotch region extending between said front and rear waist regions, said front and rear waist regions having a body facing surface and an undergarment facing surface opposed to said body facing surface, said diaper being contoured by front and rear end zones extending in parallel to each other in a waist-surrounding direction and transversely opposite lateral zones extending in parallel to each other in back-and-forth direction crossing said waist-surrounding direction, said transversely opposite lateral zones in one of said front and rear waist regions being formed with first wings extending in said waist-surrounding direction, said first wings are respectively provided on said body facing surface with first fastener means and said undergarment facing surface in the other of said front and rear waist regions being provided with second fastener means on which said first fastener means may be detachably anchored, said disposable diaper further comprising: said first wings being elastically stretchable in said waist-surrounding direction and said undergarment facing surface in said other waist region being provided in a vicinity of said second fastener means with anti-slip zones each adapted to come in contact with said body facing surface of said wings and to exhibit an average kinetic frictional force of 0.5 N or higher under a load of 58.23 g/9 cm$^2$ and an average kinetic frictional force of 5 N or lower under a load of 340 g/9 cm$^2$ relative to said body facing surface as said first fastener means being anchored on said second fastener means;

wherein elastic fibers made of a plastic elastomer and having a fiber length of 5 to 100 mm are mixed with inelastic fibers made of a thermoplastic material having a fiber length of 5 to 100 mm in said anti-slip zones.

2. The disposable diaper according to claim 1, wherein said anti-slip zones are formed so as to be placed aside from said lateral zones toward a center line bisecting a width of said diaper; said diaper further comprising, between respective said anti-slip zones and respective said lateral zones, slip-zones each exhibiting an average kinetic frictional force lower than said average kinetic frictional force exhibited by each of said anti-slip zones.

3. The disposable diaper according to claim 1, wherein a weight ratio of said elastic fibers and inelastic fibers in each said anti-slip zone is in a range of 8:2 to 5:5.

4. The disposable diaper according to claim 3, wherein said anti-slip zone comprises a mixture of said elastic fibers and inelastic fibers bonded to a sheet material which is any one of a nonwoven fabric, a woven fabric and a film.

5. The disposable diaper according to claim 4, wherein said inelastic fiber and said sheet material, which is the nonwoven fabric, contain thermoplastic material having substantially the same melting points.

6. The disposable diaper according to claim 1, wherein said lateral zones are partially broadened in said waist-surrounding direction to form second wings in said other waist region and said anti-slip zones are formed so as to be placed aside from distal end portions of said second wings toward said center line bisecting the width of said diaper.

7. The disposable diaper according to claim 6, wherein said second wing is provided in a zone placed aside to said distal end portion with a slip-zone having said average kinetic frictional force lower than that of said anti-slip zone.

8. A disposable diaper, comprising: a main portion comprising a front waist region, a rear waist region and a crotch region extending in a longitudinal direction of said diaper between said front and rear waist regions, said main portion further comprising an inner surface adapted to face a wearer in use and an outer surface adapted to face away from the wearer in use; a pair of wing portions extending outwardly in a transverse direction of said diaper from transversely opposite sides of said main portion in one of said waist regions, each of said wing portions comprising an inner surface adapted to face the wearer in use and an outer surface adapted to face away from the wearer in use, each of said wing portions further comprising a distal end and a proximal end which is closer to the respective one of the transversely opposite sides of said main portion than the distal end; fastening elements on the inner surfaces and at the distal ends of said wing portions, the proximal ends of said wing portions being free of said fastening elements; a landing zone on the outer surface of said main portion in the other of said waist regions, said fastening elements being releasably attachable to said landing zone for attaching said waist regions together; and antislip zones on the outer surface of said main portion in the other of said waist regions and on opposite sides of said landing zone, said antislip zones being contactable with predetermined areas of the inner surfaces of the proximal ends of said wing portions, when said wing portions are attached to said landing zone, to resist relative movement between the predetermined areas of the proximal ends of said wing portions and the other of said waist regions; wherein the antislip zones comprise a mixture of elastic fibers made of a plastic elastomer and inelastic fibers made of a thermoplastic material.

9. The disposable diaper according to claim 8, wherein said transversely opposite lateral zones in said crotch region are provided with leg elastic members extending further into said front and rear waist regions and said anti-slip zones are formed so as to cover parts of said leg elastic members or so as to lie on respective extensions of said leg elastic members in said longitudinal direction.

10. The disposable diaper according to claim 8, wherein said elastic fibers are continuous elastic fibers and said inelastic fibers are continuous inelastic fibers; a weight ratio of said elastic fibers and inelastic fibers in each said anti-slip zone is in a range of 8:2 to 5:5; said mixture of said elastic fibers and inelastic fibers is bonded to a nonwoven fabric that defines the outer surface of said main portion in the other of said waist regions; and said inelastic fiber and said nonwoven fabric contain thermoplastic materials having substantially the same melting points.

11. The disposable diaper according to claim 8, wherein a weight ratio of said elastic fibers and inelastic fibers in each said anti-slip zone is in a range of 8:2 to 5:5; said mixture of said elastic fibers and inelastic fibers is bonded to a nonwoven fabric that defines the outer surface of said main portion in the other of said waist regions; and a plastic ingredient of said non-woven fabric is exactly the same as that of said inelastic fibers.

12. A disposable diaper, comprising: a main portion comprising a front waist region, a rear waist region and a crotch region extending in a longitudinal direction of said diaper between said front and rear waist regions, said main portion further comprising an inner surface adapted to face a wearer in use and an outer surface adapted to face away from the wearer in use; a pair of wing portions extending outwardly in a transverse direction of said diaper from transversely opposite sides of said main portion in one of said waist regions, each of said wing portions comprising an inner surface adapted to face the wearer in use and an outer surface adapted to face away from the wearer in use, each of said wing portions further comprising a distal end and a proximal end which is closer to the respective one of the transversely opposite sides of said main portion than the distal end; fastening elements on the inner surfaces and at the distal ends of said wing portions, the proximal ends of said wing portions being free of said fastening elements; a landing zone on the outer surface of said main portion in the other of said waist regions, said fastening elements being releasably attachable to said landing zone for attaching said waist regions together; antislip zones on the outer surface of said main portion in the other of said waist regions and on opposite sides of said landing zone, said antislip zones being contactable with the inner surfaces of the proximal ends of said wing portions when said wing portions are attached to said landing zone; and slip zones on the outer surface of said main portion in the other of said waist regions, each of said antislip zones being positioned in said transverse direction between one of the slip zones and the landing zone, said slip zones being also contactable with the inner surfaces of the proximal ends of said wing portions when said wing portions are attached to said landing zone; wherein a kinetic friction coefficient between the antislip zones and the inner surfaces of the proximal ends of said wing portions is greater than that between the slip zones and the inner surfaces of the proximal ends of said wing portions; and wherein each of the antislip zones comprises a fibrous mixture of elastic fibers and inelastic fibers.

13. The diaper of claim 12, wherein the wing portions are elastically stretchable in the transverse direction; and when the inner surfaces of the proximal ends of the wing portions come into contact with the antislip and slip zones at first and second areas, respectively, the greater kinetic friction coefficient exhibited by the antislip zones provides resistance to movement of the first area of said wing portions relative to the other of said waist regions, whereas the lower kinetic friction coefficient exhibited by the slip zones allows the second area of said wing portions to be stretchable in the transverse direction thereby enhancing fitting of the diaper around the wearer's waist.

14. The diaper of claim 13, wherein the slip zones comprise said inelastic fibers and are free of said elastic fibers.

15. The diaper of claim 13, further comprising strip members attached to the transversely opposite sides of the main portion in the other of said waist regions, each said strip members comprising a base body having a first region and a second region, said second region defining one of the slip zones; and the fibrous mixture bonded to the first region but not to the second region of said base body, said fibrous mixture defining one of the antislip zones.

16. The diaper of claim 15, wherein said base body, including, said second region, comprises a non-woven fabric of the inelastic fibers and is free of said elastic fibers.

17. The diaper of claim 15, wherein each of the proximal ends of the wing portions comprises
a base elastic layer elastically stretchable in the transverse direction; and a fibrous layer of inelastic fibers disposed on said base elastic layer to define the inner surface of said proximal end of the wing portion, said fibrous layer exhibiting the greater kinetic friction coefficient with the fibrous mixture of the respective antislip zone than with the base body of the respective slip zone.

18. The diaper of claim 13, further comprising strip members attached to the outer surface of the main portion at the transversely opposite sides thereof in the other of said waist regions, each of said strip members defining one of the slip zones and one of the slip zones; wherein the kinetic friction coefficient between the antislip zones and the first areas of the wing portions is greater than that between said first areas and the outer surface of said main portion in the other of said waist regions.

19. The diaper of claim 8, further comprising strip members attached to the outer surface of the main portion at the transversely opposite sides thereof in the other of said waist regions, each of said strip members defining one of the slip zones; wherein a kinetic friction coefficient between the antislip zones and the predetermined areas of the proximal ends of said wing portions is greater than that between said predetermined areas and the outer surface of said main portion in the other of said waist regions.

20. The disposable diaper according to claim 17, wherein the elastic fibers have a fiber length of 5 to 100 mm and the inelastic fibers have a fiber length of 5 to 100 mm; and a weight ratio of said elastic fibers and inelastic fibers in each said anti-slip zone is in a range of 8:2 to 5:5; said base body is a nonwoven fabric; and a plastic ingredient of said non-woven fabric is exactly the same as that of said inelastic fibers.

* * * * *